US005377686A

United States Patent [19]

O'Rourke et al.

[11] Patent Number: 5,377,686
[45] Date of Patent: Jan. 3, 1995

[54] APPARATUS FOR DETECTING LEAKAGE FROM VASCULAR TISSUE

[75] Inventors: James F. O'Rourke, Farmington; Robert H. Fagan, Middletown, both of Conn.

[73] Assignee: The University of Connecticut, Farmington, Conn.

[21] Appl. No.: 775,284

[22] Filed: Oct. 11, 1991

[51] Int. Cl.⁶ .......................... A61B 6/00; A61B 5/00
[52] U.S. Cl. .................... 128/665; 128/633; 607/93
[58] Field of Search ............... 128/395, 633, 664, 665, 128/6

[56] References Cited

U.S. PATENT DOCUMENTS

| | | |
|---|---|---|
| 3,643,097 | 2/1973 | Uoki et al. |
| 3,830,222 | 8/1974 | Chance |
| 4,178,917 | 12/1979 | Shapiro |
| 4,200,362 | 4/1980 | Pomerantzeff |
| 4,236,526 | 12/1980 | Richard |
| 4,336,809 | 6/1982 | Clark |
| 4,350,163 | 9/1982 | Ford, Jr. et al. |
| 4,412,543 | 11/1983 | Vassiliadis et al. |
| 4,569,354 | 2/1986 | Shapiro et al. |
| 4,573,778 | 3/1986 | Shapiro |
| 4,655,225 | 4/1987 | Dähne et al. ............ 128/664 X |
| 4,838,683 | 6/1989 | Ichihashi et al. ............ 128/633 X |
| 4,842,401 | 6/1989 | Maurice ............ 128/633 X |
| 4,848,349 | 7/1989 | Sherman et al. |
| 4,852,987 | 8/1989 | Lohmann |
| 4,854,692 | 8/1989 | Kobauashi |
| 4,854,693 | 8/1989 | Ichihashi et al. ............ 128/633 X |
| 4,863,261 | 9/1989 | Flammer |
| 4,895,156 | 1/1990 | Schulze ............ 128/633 X |
| 4,900,145 | 2/1990 | Akiyama ............ 128/633 X |
| 4,932,934 | 6/1990 | Dougherty et al. ............ 128/395 X |
| 5,022,757 | 6/1991 | Modell ............ 128/633 |
| 5,062,431 | 11/1991 | Potter ............ 128/395 X |
| 5,115,137 | 5/1992 | Andersson-Engels et al. .... 128/633 X |
| 5,145,863 | 9/1992 | Dougherty et al. ............ 128/395 X |

OTHER PUBLICATIONS

Turk et al., "Clinical Indocyanine Green Fluoroescence Angiography of the Cheroidal Circulation", The British Journal of Photography, 8 Sep. 1978, pp. 727–779.
O'Rourke et al. "Fluorescein Appearance Time Curves" (Archives of Opthalmology—Nov. 1982, vol. 100).
McLaren et al. "A Scanning Ocular Spectrofluorophotometer" (Investigative Ophthalmology & Visual Science—Aug. 1988).
McLaren et al. "A Two-Dimensional Scanning Ocular Fluorophotometer" (Mayo Clinic–Feb. 1985).

Primary Examiner—David Isabella
Assistant Examiner—Elizabeth M. Burke
Attorney, Agent, or Firm—Chilton, Alix & Van Kirk

[57] ABSTRACT

An apparatus and method for directly imaging fluorophores in tissue or fluid. The apparatus includes a fluorescence exciter light source for generating fluorescence exciter light, a collimater for collimating and directing the light onto the material, and a filter between the material and a camera or the examiner's eye for passing selected wavelengths of light to the camera or to the examiner's eye. The apparatus is useful for detecting leakage in vascular eye tissue, particularly leakage from iris capillaries into surrounding tissues or into the anterior chamber of the eye.

18 Claims, 3 Drawing Sheets

APPARATUS FOR DETECTING LEAKAGE FROM VASCULAR TISSUE

BACKGROUND OF THE INVENTION

The present invention relates to fluorometry and more particularly relates to a fluorometer and a corresponding method for examining vascular tissue and fluid or tissue proximate to the vascular tissue.

Fluorometers are used for examination of various parts of the eye, including the cornea, aqueous, vitreous and retina. Typical fluorometry involves the administration of a flourescent dye to impart fluorescence to eye tissues, followed by examination of the eye through a lens system. The lens system is used in conjunction with a light source that is directed into the eye to excite the dye and to fluoresce the tissues and fluids which have absorbed the dye. Some fluorometers are attached to microprocessors that collect data and provide output indicative of certain conditions in the eye.

There are several significant drawbacks to known fluorometers used for examination of an eye. Most fluorometers require long measurement or recording periods of about 60 minutes, followed by complex analysis. Many require physical contact with the eye, which may result in discomfort to the patient. Most known fluorometers require operation by an ophthalmologist, optometrist or trained technician. Those which include microprocessors are complex and costly. Furthermore, many fluorometers require frequent calibration in order to generate useful diagnostic information. Most importantly, known fluorometers are primarily designed for diagnosing retinal eye diseases or retinal manifestations of general systemic diseases. Thus, they are not well suited for the diagnosis of iris or ciliary uveal vascular changes that signal a variety of systemic vascular disorders, i.e., disorders that are not specific to the eye and are treated by general medical physicians.

SUMMARY OF THE INVENTION

An object of the invention is to provide an apparatus and method for detecting any of a variety of systemic vascular diseases and eye diseases in a patient by observing leakage from vascular tissue in the anterior regions of the eye after administering a fluorescent material to the patient.

Another object of the invention is to provide a highly sensitive fluorometer that does not use complex computerized equipment.

Another object of the invention is to provide a fluorometer that will photographically record the fluorescence of selective biological tissue and fluid.

Yet another object of the invention is to provide a fluorometer having a sensitivity sufficient to visually detect leakage from vascular tissue into the anterior regions of the eye.

Another object of the invention is to provide a fluorometer useful to determine rates and patterns of leakage from vascular tissue.

A further object of the invention is to provide a fluorometer which does not require physical contact with the tissue or fluid being examined.

Yet another object of the invention is to provide a fluorometer for use by a variety of physicians and trained professionals in and outside the fields of ophthalmology and optometry.

Other objects will be in part obvious and in part pointed out more in detail hereinafter.

The invention in a preferred form is an apparatus for directly recording light emitted by fluorophores located within or proximate to vascular tissue. The apparatus includes a fluorescence exciter light source for generating exciter light to be directed onto the fluorophore-containing tissue or fluid being examined, a light conduit for collimating and directing the exciter light source, and a barrier filter for maximizing the passage therethrough of light emitted by the fluorescing tissue or fluid, and minimizing the passage therethrough of light having a wavelength equivalent to the wavelength of the exciter light source. The apparatus optionally further comprises direct light recording means such as a camera suitably positioned for recording fluorescence of the tissue or fluid. Alternatively, the fluorescence of the tissue or fluid can be viewed directly by the examiner through the filter, with or without a magnifying loupe. The invention is particularly useful for detecting leakage of blood from vascular tissue in the anterior regions of the eye, i.e., regions in front of the vitreous, including the anterior chamber, iris, cornea, and conjunctiva, into nearby tissue or fluid. Preferably, when fluorescein is used as the fluorescent agent which is detected, the fluorescence exciter light source is a blue laser, and the barrier filter is a long wave pass filter which will transmit light having a wavelength of about 500–515 nm or more. When a direct light recording means is used, it preferably is a 35 mm camera.

The apparatus of the invention is useful for in vivo, non-surgical examination of vascular tissue and/or tissue or fluid proximate to vascular tissue in order to detect a variety of vascular diseases, including but not limited to diabetes, vasculitis, hypertension and arteriosclerosis, as well as primary eye diseases affecting the conjunctiva, anterior chamber, cornea, iris, lidskin and other parts of the anterior region of the eye. The preferred method of examination comprises administering to the bloodstream of the patient a flourescent dye, directing a fluorescence exciter light source onto selected vascular tissue of the patient or onto tissue or fluid proximate to the vascular tissue, and either directly recording the fluorescence of the illuminated tissue or fluid using a camera having a filtered lens, or directly viewing the leakage through an appropriate filter, with or without the use of a magnifying loupe. When images are photographically recorded, they can be analyzed qualitatively by inspection, or quantitatively, such as by using a conventional densitometer.

The invention accordingly consists in the features of construction, combination of elements and arrangement of parts which will be exemplified in the construction hereafter set forth and the scope of the application which will be indicated in the appended claims.

DETAILED DESCRIPTION OF THE INVENTION

Figure 1:
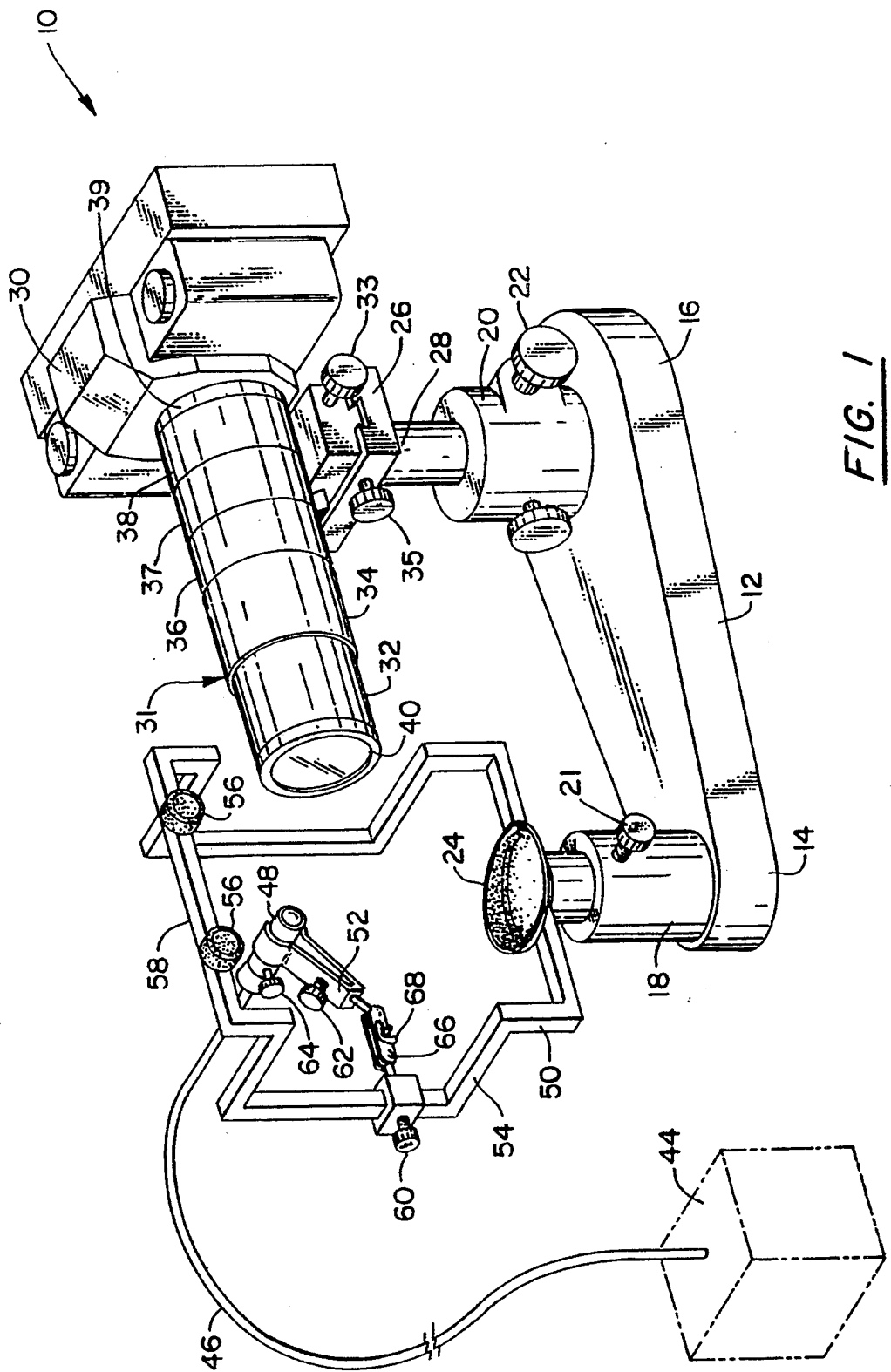
FIG. 1 is a schematic, front perspective view of a fluorometer according to the present invention, adapted for examining a human eye by photographically recording images of the eye.

Referring now to the drawings in detail wherein like numerals represent the same or like parts throughout, and referring particularly to FIG. 1, a fluorometer 10 according to a preferred embodiment of the invention is shown. The fluorometer 10 is sufficiently sensitive to detect fluorophores located within or leaking from vascular tissue in a human eye, particularly to detect leakage from iris capillaries into surrounding iris tissues and into the aqueous humor contained in the anterior chamber of the eye. The fluorometer 10 has a heavy, horizontal platform base 12 with opposite first and second end portions 14,16, respectively, from which first and second support bars 18,20, respectively, extend vertically upward. The base 12 and support bars 18,20 can be similar to those used for other types of apparatus adapted for examining an eye. The height of each support bar, and thus the height of the components mounted thereon, is vertically adjustable by suitable means, such as by rotating the first support bar adjustment knob 21 and the second support bar adjustment knob 22 shown in FIG. 1.

A chin rest 24 having a concave shape adapted to support the chin of a patient is rotatably mounted on the upper end of the first support bar 18. The chin rest 24 can be horizontally rotated around a central axis by temporarily loosening the first support bar adjustment knob 21 shown in FIG. 1 and then manually rotating the chin rest 24. An adjustable camera mount assembly 26 or other appropriate camera mounting means is attached to the upper end 28 of the second support bar 20, and a camera 30 is secured on the upper surface thereof. The lens 32 of the camera 30 is positioned at a height and aimed in a direction appropriate to focus, from the side, upon the eye of a patient whose chin is resting in the chin rest 24. The final horizontal position of the camera 30 can be adjusted bidirectionally by suitable means, such as by rotating the forward-back adjustment knob 33 and left-right adjust knob 35 shown in FIG. 1.

A preferred camera 30 according to the invention is a 35 mm camera with an instant developing-type backing and a tube extended, fast, wide aperture photographic lens assembly 31. A fast lens, preferably with a F stop of 1.9 or lower, more preferably about 1.2, is used in order to pass a large amount of light. The extension tubes provide magnification of the eye in order to facilitate analysis of the eye. One advantage of instant developing film is that images are produced in a matter of minutes. Another advantage is that instant film is available that allows halves of single frames to be exposed in sequence to provide two side-by-side exposures taken at different times, e.g., at intervals of 60 seconds, thus providing a convenient indication of the rate of capillary leakage. However, the camera alternatively can be a conventional 35 mm camera, an instant developing camera, a video camera, or a 35 mm camera having a reflex back, such as a 2"×2" reflex.

Highly light sensitive, fast, fine grain emulsion film preferably is used with the camera in order to obtain photos suitable for diagnosing abnormalities in the vascular tissue of the patient within a short period of time after the dye is administered. Black and white film rated A.S.A. 3200 has been found useful, as well as instant developing black and white film rated A.S.A. 3000. Conventionally developed film generally provides slightly higher sensitivity, and therefore is preferred over instantly developed film when the images are to be quantitatively analyzed with a densitometer.

The combination of various features of the invention, including the light source, filter, lens and film, contributes to the high sensitivity of the apparatus. According to the preferred embodiment, the system has a sensitivity sufficient to image concentrations of fluorophores of $10^{-8}$ g/ml or more in the anterior region of an eye.

In the preferred embodiment shown in FIG. 1, the camera 30 has a lens assembly 31 including a cylindrical, wide aperture, fast lens 32 mounted to a first outer extension tube 34, which is in turn attached to a second extension tube 36. Second extension tube 36 is attached to a third extension tube 37, which is in turn attached to a fourth extension tube 38. Fourth extension tube 38 is mounted to the camera in a conventional manner using an adapter 39. The lens 32 is telescopically adjustable inward and outward relative to the outer extension tube 34.

A relatively flat, cylindrical filter 40 is mounted to the outer end of the lens 32. The filter 40 includes a holder which is threaded to the lens 32 in a conventional manner. The lens of the filter 40 is retained in the holder by an O-ring (not shown). An appropriate filter is selected such that it transmits light having a wavelength equivalent to the emission fluoroescence of a dye that is administered to the patient, and excludes the wavelengths emitted by the exciter light source. When a blue laser light source is used in conjunction with fluorescein, which has been found to provide an emission in the range of 500–560 nm and maximal emission at about 525 nm, particularly useful filters are long wave pass filters which only transmit light having a wavelength greater than or equal to about 500–520 nm. Alternatively, interference filters which transmit light within a particular range, for example 500–560 nm, and exclude light having higher and lower wavelengths, also will produce good results.

The fluorometer 10 of the invention includes a light source 44 which emits light that is directed into an eye of a patient. The light is adapted to shine into the patient's eye during the times at which images are actually being recorded, and is adapted to be occluded between recording intervals in order to prevent unnecessary exposure. The light source 44 includes light having a wavelength and intensity appropriate to excite the fluorophores in the subject tissue or fluid to a degree sufficient to be detected by the film in the camera. The preferred light source 44 according to the invention, used in conjunction with fluorescein, is a 400–500 nm laser, and more preferably is a 485–490 nm laser. The intensity of the light source preferably is about 0.5–6 mW, or more preferably 1–3 mW. The light is in the form of a beam which has a diameter that is preferably about 5–20 nm, or more preferably 10–15 mm at the point of contact with the eye. When the diameter of the beam is narrowed to be less than 5–10 mm, it may be necessary to reduce the intensity of the beam to avoid unnecessary exposure. On the other hand, if the beam diameter is increased, for example, up to about 25 mm, it may be possible to use a higher intensity beam without raising safety concerns. When fluorescein, which is excited at about 490 nm, is used as the fluorescent dye, the inventors have found that a pure blue 488 nm Argon ion laser at an intensity of about 3 mw and a beam diameter of about 12 mm at the point of contact with the eye provides particularly favorable results. As shown in FIG. 1, the laser preferably is transmitted through a single core fiberoptic cable 46.

In the preferred embodiment, the exit end of the cable 46 is connected to a cylindrical collimater 48 which condenses or focuses the laser beam, preferably to a width of between 1 and 25 nm, and directs the beam onto the selected tissue or fluid. The diameter of the beam is adjusted by rotating the collimater adjustment knob 64. A 12 mm beam diameter is particularly preferred when the anterior chamber of the eye is to be examined, as it will illuminate the entire anterior chamber at one time. The collimater 48 is mounted to a collimater mounting frame 50, with the collimater directing the light into the eye of a patient whose chin is resting on the chin rest. The collimater mounting frame 50 is mounted to the first support bar 18, and preferably is rotatable relative to the first support bar 18. Preferably, the light is shone straight into the patient's eye from directly in front of the patient.

As shown in FIG. 1, the collimater 48 is mounted to the collimater mounting frame 50 using an adjustable collimater clamping device 52. The collimater clamping device 52 can be any clamping means which is capable of supporting the collimater 48 and directing the light source 44 into the eye. Preferably, the clamping device 52 is adjustable in order to place the light source at any of a variety of positions relative to the eye. In FIG. 1, an adjustable, tweezer-like clamping device 52 is shown surrounding the outer circumference of the collimater 48 on a pair of opposite sides. The tightness of the clamping device 52 around the collimater 48 can be adjusted by rotating a clamp adjustment knob 62.

The clamping device 52 is pivotally connected to one end of an elongated clamp arm 66. The end of the clamp arm 66 opposite the clamping device 52 has a sleeve which slidably fits around the collimater mounting frame 50. The sleeve is pivotable relative to the remainder of the clamp arm 66. The clamping device 52 is pivotably fixed relative to the clamp arm 66 by tightening a bolt and wing nut assembly 68. The sleeve of clamp arm 66 is slidably fixed to the collimater mounting frame 50 by tightening sleeve knob 60.

The collimater mounting frame 50 is constructed to enable an operator to adjustably direct the light source 44 into the eye of a patient from any of a variety of different angles, and to allow the camera to photograph the eye from various angles. In the embodiments shown in FIGS. 1 and 2, the collimater mounting frame 50 is generally rectangular and vertical, however, it has a pair of sideways-U-shaped recessed portions 54 on the vertical side portions of the frame. The sideways-U-shaped recessed portions 54 extend parallel to each other, outward in a direction opposite to where the patient is positioned and perpendicular to the remainder of the collimater mounting frame 50, thereby enabling photographs to be taken when the camera 30 is positioned to the side of the patient. A pair of cylindrical forehead rest pads 56 are mounted horizontally relative to each other on a horizontal top portion 58 of the frame, against which the forehead of a patient is placed. It is noted that the collimater 48 can have other shapes and forms which allow for adjustable placement of the collimater and camera relative to each other and to an eye.

FIG. 1 illustrates an arrangement in which the light source 44 is in front of the eye and the camera 30 is to the side of the eye. This arrangement is particularly useful for examination of the aqueous humor in the anterior chamber, as images of the aqueous humor can be recorded without concurrently recording images of the iris in the background.

Figure 2:
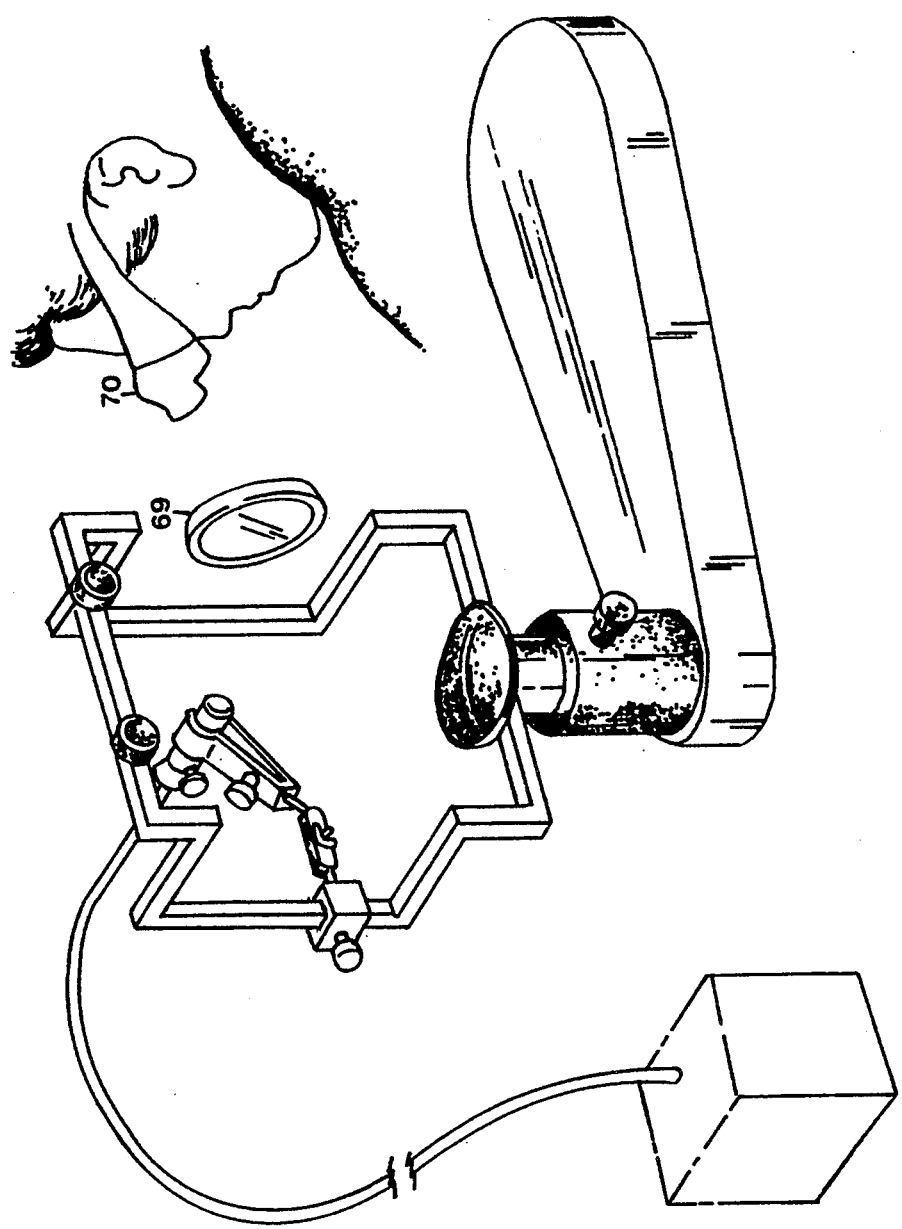
FIG. 2 is a schematic, front perspective view of a fluorometer according to the invention, adapted for directly visualizing leakage in the anterior chamber of the human eye.

FIG. 2 illustrates an arrangement useful for direct visualization of leakage from vascular tissue into the anterior chamber of an eye. The apparatus is the same as that shown in FIG. 1 except that the camera and its first support bar 20 are removed, and the filter 40 is held by the examiner, several inches away from the eye, as he directly views the eye from the side in a darkened room. Preferably, the examiner uses a 2X-4 X magnifying loupe 70 to see the leakage in greater detail, however, use of a magnification device is not required when the combination of the light exciter source and the filter render the apparatus sufficiently sensitive to detect leakage without magnification. The filter 40 can be combined with the magnifying loupe 70 as a binocular spectacle. This frees the examiner's hand to be used to further open the patient's eyelid. Direct visualization has been found to be particularly effective when a long wave pass filter passing light having a wavelength of about 500 nm or more, more preferably 515 nm or more, is used in conjunction with fluorescein and an argion ion laser, and is particularly useful as a primary screening technique.

Figure 3:
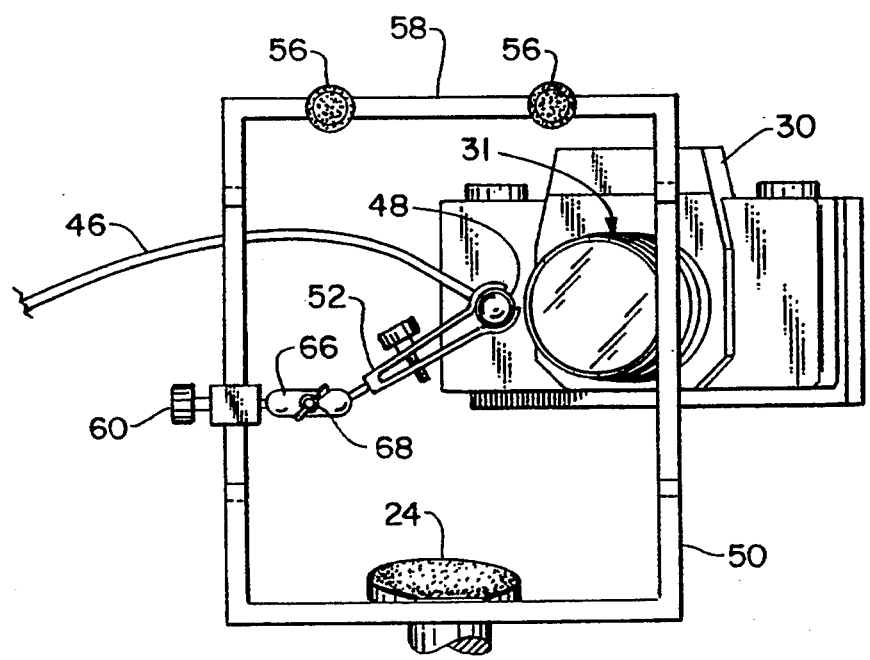
FIG. 3 is a fragmentary, schematic front view of the fluorometer shown in FIG. 1, the camera having been rotated to be positioned in front of the eye, next to the exciter light collimater.

FIG. 3 illustrates an alternative arrangement of the apparatus shown in FIG. 1. In FIG. 2, the chin rest 24 and collimater mounting frame 50 have been rotated approximately 90° relative to the arrangement shown in FIG. 1. The collimater 48 is positioned next to the camera 30, with the light source 44 aimed directly into the front of a patient's eye. This orientation can be used to detect patterns of fluorescence in blood vessels of the iris and/or conjunctiva, and to detect leakage of dye from such vessels, particularly in blue-eyed patients and in other situations in which iris background is not a problem.

The apparatus described above is used to practice the preferred method of the invention. This method comprises intravenously administering to a patient a suitable dosage of fluorescein or another appropriate fluorescent agent, e.g., indocyanin green. The dye can also be used in drop form to observe pattern changes on the eye surface. Preferably, the intravenous dosage for an average adult patient is about 0.25 to 0.5 grams of fluorescein administered, for example, as 1.0 ml of a solution containing 25% fluorescein, or 5.0 ml of a solution containing 10% fluorescein. Using the apparatus of the invention, leakage of fluorescein from the vascular tissue into the anterior regions of the eye of a diseased patient can be detected within about 1 minute after the fluorescein reaches the eye tissues. In contrast, for a healthy patient, leakage from the vascular tissues in the anterior region of the eye ordinarily will not be detected for about 5-10 minutes after the fluorescein has been administered. Thus, in order to determine whether or not a patient has a vascular disorder, within about a minute of administration of the dye, the patient is positioned with his/her chin in the chin rest 24, and the light source 44 is directed into one of the patient's eyes. In the embodiment illustrated in FIGS. 1 and 3, the camera 30 is positioned to record images of the eye. The light source 44 is shone intermittently into the eye while pictures are taken of the anterior chamber or another portion of the anterior region of the eye, or while the examiner views the eye. When a camera is used, images are recorded for exposure periods of up to about 10 or 15 seconds, but preferably about 1 to 3 seconds, at known intervals for a period of time sufficient for a physician or other appropriately trained professional to determine the rate of build-up of fluorescein in the fluid or tissue, and/or to determine whether a vascular disorder is present. Generally, images are recorded for a minimum of about 5 minutes. A photo or a view of the other eye is then taken to help differentiate between local eye conditions and systemic diseases. If the amount of leakage in the two eyes is unequal, it is likely that excess leakage in one eye was caused by a localized eye disorder, such as inflammation or a tumor. On the other hand, excess leakage in both eyes is indicative of a systemic disease. The method of detecting leakage by direct observation using the apparatus of FIG. 2 is essentially the same except that the examiner's eye is substituted for the camera and the filter is hand-held by the examiner.

When instant developing film is used, or the eye is viewed directly, a decision to terminate the recording process in more or less than 5 minutes can be made by examining the photographs as they develop, or by actual observation of the eye. Conventional fluorometers typically require 60 minutes to record leakage of intravenously administered dye into the eye, and thus the invention substantially reduces the time requirements for obtaining meaningful information. As mentioned above, for preliminary screening purposes prior to using photography, the eye can be viewed directly by the examiner as shown in FIG. 2, and if it appears that a vascular disorder is present, further examination can be conducted using the photographic apparatus of FIGS. 1 and 3.

Fluorescein dye also can be administered orally. Recommended oral dosage is about 0.5–2 grams of fluorescein given in a citrous drink. However, one of the advantages of injecting the fluorescein intravenously as contrasted to administering it orally is that detectable quantities of fluorescein will reach various parts of a patient's body, including the vascular tissue in the eyes, more rapidly when an intravenous injection is administered.

The apparatus of the invention is not invasive, as it does not require the use of a contact lens which directly contacts the eye similar to that which is required with many conventional devices for eye examination. The fluorometer is simple to operate, and can be used by any type of physician, as well as by a variety of other trained professionals. The photographs or negatives obtained can be analyzed visually, or can be quantified using a conventional densitometer. The apparatus can be modified to include several cameras, e.g., one which views the eye from the front and another which simultaneously views the eye from the side, or to use one or more cameras in combination with direct visualization. The apparatus can be used to examine parts of the anterior region eye other than the anterior chamber or iris, e.g., the cornea, conjunctiva, and lidskin. Various configurations of the fluorometer can be used to examine other bodily tissues and fluids, and also can be used to examine various biological specimens, or inanimate fluorescent materials such as rocks and minerals.

EXAMPLE

A patient was intravenously administered 1.0 ml of a solution containing 25% fluorescein. Within a minute after administration, the patient's right eye was exposed to a 4 mW, 488 nm Argon ion laser beam, the laser being directed into the patient's eye from several inches away, directly in front of the eye, normal to the surface plane of the colored iris, for about 2–3 seconds each minute for several minutes. A collimater was used to control the diameter of the beam such that the width of the beam upon contact with the eye was 12 mm. A 35 mm camera having several extension tubes, a long wave pass filter which allows for the passage of light having a wavelength greater than or equal to 500 nm, and highly sensitive instant-developing film in an instant developing attachment, as illustrated in FIG. 1, was positioned to the side of the eye along a path with the eye which formed a 90° angle relative to the path of the laser beam into the eye. Photographs were taken at intervals of 60 seconds for a period of 5 minutes using a one second exposure time, the pictures being taken during periods of illumination of the eye with the Argon laser. After the photographs were developed, they were analyzed with a densitometer. Mathematical calculations showed that amounts of fluorescein entering the anterior chamber increased at a rate of about 25% per minute, thus indicating that the patient probably has a vascular disorder that has damaged blood vessels in the iris region, assuming that the patient's other eye has a comparable rate of leakage.

As will be apparent to persons skilled in the art, various modifications and adaptations of the apparatus and method described above will be come readily apparent without departure from the spirit and scope of the invention, the scope of which is defined in the appended claims.

What is claimed is:

1. An apparatus for detecting leakage from vascular tissue located in an anterior region of an eye into aqueous humor, comprising:

positioning means for maintaining the eye in a generally stationary position, fluorescence exciter light generation means for generating fluorescence exciter light at a fluorescence exciter light wavelength, light conduit means connected to the fluorescence exciter light generation means for directing the fluorescence exciter light onto the aqueous humor, direct light recording means for directly recording fluorescence of the aqueous humor, the direct light recording means being positioned for recording light emitted from a side of the aqueous humor, and barrier filter means disposed between the eye and the direct light recording means for maximizing passage to the recording means of light having a first wavelength which is the wavelength of light emitted from the aqueous humor, and minimizing passage to the recording means of light having a second wavelength, the second wavelength including the fluorescence exciter light wavelength.

2. An apparatus according to claim 1 wherein the fluorescence exciter light generation means comprises a laser for generating fluorescence exciter light at a wavelength of 400–500 nm, and the direct light recording means comprises a camera.

3. An apparatus according to claim 2, wherein the fluorescence exciter light which is collimated in the light conduit means forms a beam having a diameter of about 5–20 mm upon contact with the eye at an intensity of 0.5–6 mW.

4. An apparatus according to claim 1, wherein the fluorescence exciter light generation means comprises a laser for generating fluorescence exciter light at a wavelength of 485–490 nm.

5. An apparatus according to claim 4, wherein the direct light recording means comprises a camera.

6. An apparatus according to claim 1, further comprising a densitometer for quantifying fluorescence of the tissue which is recorded by the direct light recording means.

7. An apparatus according to claim 1, wherein the barrier filter means comprises a long wave pass filter, the first wavelength consists of wavelengths greater than or equal to about 500–520 nm, including a minimum first wavelength, and the second wavelength consists of wavelengths less than the minimum first wavelength.

8. An apparatus according to claim 1, wherein the first wavelength consists of wavelengths greater than or equal to about 500 nm, and the second wavelength consists of wavelengths less than about 500 nm.

9. An apparatus according to claim 1, wherein the light conduit means is configured to direct the fluorescence exciter light along a first linear path and the direct light recording means is configured to record light along a second linear path which is generally perpendicular to the first linear path.

10. An apparatus according to claim 9, wherein the fluorescence exciter light generation means is configured to direct fluorescence exciter light directly into the eye from in front of the eye.

11. An apparatus according to claim 1, wherein both the fluorescence exciter light generation means and the direct light recording means are positioned in front of the eye.

12. An apparatus according to claim 1, wherein the direct light recording means is configured to record light emitted from the anterior chamber of the eye.

13. An apparatus according to claim 1, wherein the fluorescence exciter light generation means is an argon laser and the direct light recording means is a camera.

14. An apparatus for directly visualizing leakage from vascular tissue located in an anterior region of an eye into aqueous humor comprising:
   positioning means for maintaining the eye in a generally stationary position,
   fluorescence exciter light generation means for generating fluorescence exciter light at a wavelength of 400–500 nm,
   light conduit means connected to the fluorescence exciter generation means for directing the fluorescence exciter light onto the aqueous humor, and
   barrier filter means positioned to the side of the eye for maximizing passage of light therethrough which is emitted from the Aqueous humor and has a first wavelength, and minimizing passage of light therethrough having a second wavelength, the second wavelength including the wavelength of the fluorescence exciter light.

15. An apparatus according to claim 14, wherein the fluorescence exciter light generation means comprises a laser for generating fluorescence exciter light at a wavelength of 485–490 nm.

16. An apparatus according to claim 17, wherein the light conduit means is configured to direct the fluorescence exciter light directly into the eye from in front of the eye along a first linear path, the apparatus further comprising direct light recording means which is configured to record light emitted from the aqueous humor along a second linear path which is generally perpendicular to the first linear path.

17. An apparatus for detecting leakage of fluorophores from vascular tissue located in an anterior region of an eye into aqueous humor comprising:
   positioning means for maintaining the eye in a generally stationary position
   fluorescence exciter light generation means comprising a laser for generating fluorescence exciter light at a wavelength of 485–490 nm,
   light conduit means connected to the fluorescence exciter light generation means for directing the fluorescence exciter light onto the aqueous humor,
   direct light recording means for directly recording fluorescence of the aqueous humor, the direct light recording means being positioned for recording light emitted from a side of the aqueous humor, and
   barrier filter means disposed between the eye and the direct light recording means for maximizing passage to the direct light recording means of light having a wavelength greater than or equal to about 500–520 nm, and excluding passage to the direct light recording means of light having wavelength of *less than about* 500 nm.

18. An apparatus according to claim 17, wherein the light conduit means is configured to direct the fluorescence exciter light directly into the eve from in front of the eye along a first linear path and the direct light recording means is configured to record light emitted from the aqueous humor along a second linear path which is generally perpendicular to the first linear path.

* * * * *

UNITED STATES PATENT AND TRADEMARK OFFICE
CERTIFICATE OF CORRECTION

PATENT NO. : 5,377,686
DATED : January 3, 1995
INVENTOR(S) : James O'Rourke et al It is certified that error appears in the above-indentified patent and that said Letters Patent is hereby corrected as shown below:

Claim 16, column 10, line 13, change "17" to --14--.

Claim 18, column 10, line 45, change "eve" to --eye--.

Signed and Sealed this

Ninth Day of May, 1995

Attest:

BRUCE LEHMAN

*Attesting Officer*     *Commissioner of Patents and Trademarks*